United States Patent [19]

Tappe

[11] 4,157,446

[45] Jun. 5, 1979

[54] 3-FORMYL-PYRIDINES AND PROCESS FOR MAKING THEM

[75] Inventor: Horst Tappe, Dietzenbach, Fed. Rep. of Germany

[73] Assignee: Cassella Aktiengesellschaft, Frankfurt, Fed. Rep. of Germany

[21] Appl. No.: 819,756

[22] Filed: Jul. 29, 1977

[30] Foreign Application Priority Data

Aug. 5, 1976 [DE] Fed. Rep. of Germany ....... 2635205
Aug. 5, 1976 [DE] Fed. Rep. of Germany ....... 2635206

[51] Int. Cl.² .................. C07D 213/69; C07D 213/76
[52] U.S. Cl. ................................. 546/296; 260/156; 542/420; 542/423; 8/42 R
[58] Field of Search ...................... 260/281 G, 281 R

[56] References Cited

U.S. PATENT DOCUMENTS 3,867,392  2/1975  Heinrich et al. .............. 260/294.812

FOREIGN PATENT DOCUMENTS 2025427 12/1971 Fed. Rep. of Germany.
741667 12/1955 United Kingdom.

OTHER PUBLICATIONS

Reeve et al., J. Org. Chem. 31, pp. 2164–2168 (1966).
Beilstein, 4th Edition, vol. 21, p. 165.
Bobbitt et al., J. Org. Chem. 25, 560 (1960).

*Primary Examiner*—Mark L. Berch
*Attorney, Agent, or Firm*—Connolly and Hutz

[57] ABSTRACT

A $\beta,\beta,\beta$-trihalo-$\alpha$-hydroxyethyl (e.g. —CHOH—CCl$_3$) group is introduced into a 2,6-dihydroxy pyridine. The 3-formyl-4-methyl-2,6-dihydroxy pyridine produced by splitting off haloform from the trihalohydroxyethyl product, is a desirable intermediate for the making of dyes and other products, and the alkali metal or alkaline earth metal salts of the formyl compound are more stable forms of this intermediate.

2 Claims, No Drawings

3-FORMYL-PYRIDINES AND PROCESS FOR MAKING THEM

The present invention relates to pyridine compounds and their preparation.

Among the objects of the present invention is the provision of novel pyridine compounds, as well as processes for preparing them and intermediates therefor.

The foregoing as well as additional objects of the present invention are more fully expounded in the following description of several of its exemplifications.

According to the present invention a formyl group or a $\beta,\beta,\beta$-trihalo-$\alpha$-hydroxyethyl group is substituted on a pyridine ring that has two hydroxy substituents in the 2,6-position. The formyl-substituted product is a particularly valuable intermediate and can be recovered in its free form or in the form of salts, particularly of alkali metal or alkaline earth metal.

It has been reported in British Patent Specification No. 741,667 that 2-amino-4-hydroxypyrimidines can have a formyl or $\beta,\beta,\beta$-trihalo-$\alpha$-hydroxyethyl group introduced into their 5-position. The introduction of the latter group is described as effected in the presence of an excess of pyridine, yet that reference contains no mention of a possible reaction with the pyridine.

It has now been discovered that a pyridine containing both 2- and 6-hydroxy substituents will undergo reactions similar to that of the British reference even though such pyridines do not have any amino substitution and accordingly have two less nitrogens.

The following examples are illustrative, all parts and percentages being by weight unless otherwise noted.

EXAMPLE 1

125 parts of 4-methyl-2,6-dihydroxy pyridine dissolved in 400 parts ethanol are mixed with a solution of 80 parts sodium acetate in 100 parts water, and a solution of 148 parts anhydrous chloral in 400 parts water. The mixture is stirred for 8 hours at 20° C., and then permitted to stand an additional 48 hours at room temperature. A precipitate forms and is then filtered off under suction, the resulting solids washed with water, and then dried at 30° C. in vacuo. There are thus recovered 218 parts (80% of theory) of 3-($\beta,\beta,\beta$-trichloro-$\alpha$-hydroxy)ethyl-4-methyl-2,6-dihydroxy pyridine, which when recrystallized from ethyl acetate shows a melting point of 195° C. Analysis of its nitrogen and chlorine contents give the following results:

|  | N % | Cl % |
| --- | --- | --- |
| Calculated | 5.4 | 39.9 |
| Found | 5.1 | 39.1 |

The 4-methyl-2,6-dihydroxy pyridine is prepared as described in the prior art.

EXAMPLE 2

272.5 parts of 3-($\beta,\beta,\beta$-trichloro-$\alpha$-hydroxy)ethyl-4-methyl-2,6-dihydroxy pyridine are introduced into 3,000 parts of ethanol and a solution of 500 parts of potassium hydroxide in 400 parts of water and 1,700 parts of ethanol is then added. The reaction mixture is boiled at atmospheric pressure under reflux for 30 minutes, with stirring, and is then cooled down to 20° C. Crystals deposit during the reaction, and after cooling of the mixture they are filtered off, washed with 200 parts of ethanol and dried. The crude product thus obtained can be freed from adhering excess potassium hydroxide by washing with 5% acetic acid until a neutral reaction is obtained from the moist crystals. 94 parts are thus obtained of potassium 3-formyl-4-methyl-2,6-dihydroxy-pyridine (=49% of the theoretical yield), which possesses a melting point of above 350° C. after recrystallization from water.

Analysis: calculated: C, 44.0%; H, 3.2%; N, 7.3%. Found: C, 44.2%; H, 3.4%; N, 7.3%.

UV and IR spectra confirm the structure.

EXAMPLE 3

The conversion of the potassium salt into the metal-free compound is carried out as follows: 19.1 parts of the crude product obtained in Example 2 are suspended in 200 parts of a mixture of 160 parts of acetic acid and 40 parts of water, and the reaction mixture is concentrated to 50 parts under vacuum, with warming. On allowing the concentrated solution to stand, the metal-free compound crystallizes out and is filtered off. The pure 3-formyl-4-methyl-2,6-dihydroxy pyridine, with a melting point of 180°–182° C., is obtained by redissolution and recrystallization from a mixture of 160 parts of ethanol and 40 parts of water.

Analysis: calculated: C, 54.9%; H, 4.6%; N, 9.1%. Found: C, 55.1%; H, 4.7%; N, 9.0%.

In the foregoing reactions the bromo analog of the chloral can replace some or all of the chloral to yield the analogous product. Also, more than one type of halogen can be contained in the molecule of such aldehyde.

The foregoing reactions with the trihaloaldehydes do not take place when benzene compounds are used in place of the pyridine compounds. Solvents other than those given in the examples can be used to dissolve the reactants.

The caustic used in the reaction that splits out the haloform can be provided by alkali metal or alkaline earth metal hydroxides or any other caustic material that brings the pH of the reaction mixture up to at least about 11 to 12. The velocity of this reaction increases with higher pH values as well as with temperature, but it can be effected at pH 11 to 12 at room temperature. Elevated temperatures such as up to 150° C. can be used to further speed this splitting, but the yields are then poorer inasmuch as the formyl-substituted product rapidly deteriorates at such elevated temperatures.

The salt forms of the compounds, such as those produced in the presence of the caustic are more stable and are preferred where significant storage or shipment of the formyl-containing intermediate is involved. The sodium, lithium, calcium and barium salts are about as effective as the potassium salt of Example 2, and are readily formed by adding the appropriate bases to the free acid of Example 3.

The free formyl compound is considered to have a structure such as

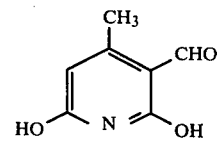

or of the tautomeric structures such as

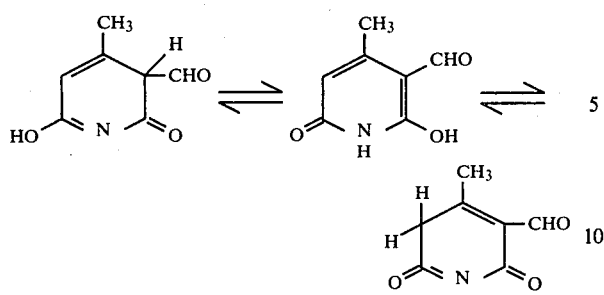

all of which tautomers are interconvertible so that they are all embraced even though only one is named.

The formyl compounds of the present invention have an unsubstituted 5-position which can be taken advantage of to make pharmaceuticals, plant protection agents or water-soluble and water-insoluble azo-dyes by coupling with diazonium compounds. They contain one strongly acidic hydrogen and their salts have one equivalent of metal replacing that hydrogen.

The following examples are typical of the use of the compounds as intermediates for the production of azo dyes by coupling with diazonium compounds, all parts and percentages being by weight unless otherwise noted:

(a) 152 parts of 2-methyl-4-nitro-aniline are diazotized in 300 parts of water with a solution of 7.7 parts sodium nitrite in 50 parts of water while adding 36.0 parts of 30% strength hydrochloric acid at 0° to +5° C. The filtered, clear diazo solution is allowed to run into a suspension of 20 parts of 2-hydroxy-3-formyl-4-methyl pyridone(6)-potassium in 400 parts of water and the reaction temperature is kept at 0° to +5° C. whilst coupling by adding 500 parts of ice. When coupling is complete, the resulting dyestuff of the formula

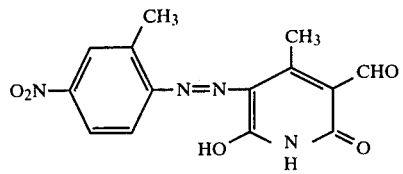

is filtered with suction, washed with water until neutral and dried. Thereafter it is converted to a dye dispersion in the conventional manner, which, if dyeing is effected in accordance with the customary methods, dyes polyester material golden yellow shades.

(b) 21.6 parts of 3-aminophenyl ester of dimethylsulfonic acid are dissolved in 280 parts of water with the addition of 36 parts of 30% strength hydrochloric acid and diazotized with a solution 7.7 parts of sodium nitrite in 50 parts of water at 0° to +5° C. If the coupling is effected as described under (a) above, a yellow dyestuff of the formula

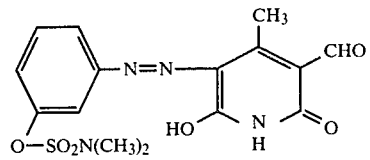

is obtained. The dyestuff dyes polyester material yellow color tones if dyeing is effected in accordance with the conventional methods.

(c) 24.9 parts of 3-aminophenyl ester of benzenesulfonic acid are dissolved in 200 parts of water with the addition of 90 parts of 35% strength hydrochloric acid and diazotized with a solution of 7.7 parts of sodium nitrite in 50 parts of water at 0° to +5° C. If coupling is effected as described under (a) above, a yellow dyestuff of the formula

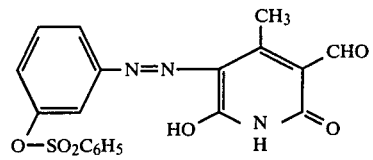

is obtained.

(d) Analogously to the procedure as depicted above, a further dyestuff of the formula

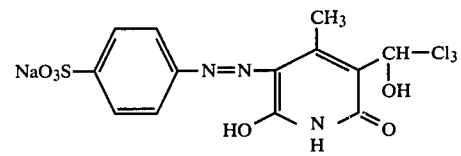

is obtained, which dyes polyamide and wool yellow color tones when dyeing is effected in accordance with the conventional methods.

The foregoing use is not available for related formyl compounds such as described in German Offenlegungsschrift No. 2,025,427 where there is no unsubstituted ring position.

Among the compounds of the present invention it is in particular the 3-formyl-4-methyl-2,6-dihydroxy-pyridine or the alkali or alkaline earth metal salts thereof that is outstandingly suited for the making of valuable metal complex compounds of the general formula

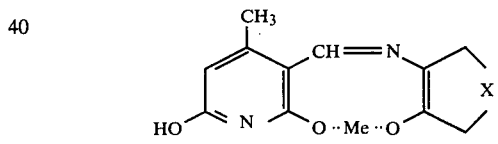

wherein X stands for

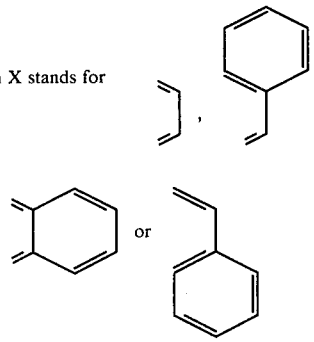

and the benzene or naphthalene ring formed by X and the remaining portion of the molecule may also be substituted by one or two substituents of the methyl, methoxy, chloro, bromo, trifluoromethyl, nitro, cyano, —$CONR_1R_2$ or —$COOR_3$ series, $R_1$ and $R_2$ standing for hydrogen or alkyl with 1 to 4 carbon atoms and $R_3$ for alkyl with 1 to 4 carbon atoms, and Me denotes a nickel, copper, zinc or cobalt atom. Copper for Me is preferred.

Metal complex compounds of the formula

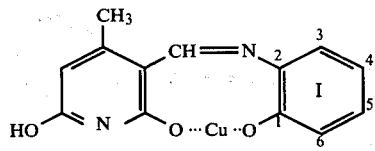

in which the benzene ring I may be substituted, as noted above, especially mono-substituted in the para-position to the oxygen, i.e. in the 4-position, are of particular interest.

The novel metal complex compounds can be made by metallizing the condensation products produced by reacting in accordance with the methods known per se, 3-formyl-4-methyl-2,6-dihydroxy-pyridine with an orthohydroxyamino compound of the general formula

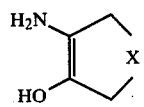

wherein X has the above meaning and the benzene or naphthalene ring may, as indicated above, be substituted.

The following orthohydroxyamino compounds, for example, are suited as reactants:
orthoaminophenol
2-amino-4-(or 3- or 5- or 6-)nitrophenol
2-amino-4-(or 3- or 5- or 6-)chlorophenol
2-amino-4-(or 3- or 5- or 6-)bromophenol
2-amino-4-(or 3- or 5- or 6-)cyanophenol
2-amino-4-(or 3- or 5- or 6-)methoxycarbonylphenol
2-amino-4-(or 3- or 5- or 6-)ethoxycarbonylphenol
2-amino-4-(or 3-)butoxycarbonylphenol
2-amino-4-(or 5-)trifloromethylphenol
2-amino-4-(or 5-)carbonamidophenol
2-amino-4-(or 5-)dimethylamidophenol
2-amino-4-(or 5-)ethylcarbonamidophenol
2-amino-1-naphthol
1-amino-2-naphthol
2-amino-4-(or 5- or 7-)chloro-1-naphthol
1-amino-4-(or 5-, 6- or 7-)chloro-2-naphthol
1-amino-3-(or 4- or 8-)nitro-2-naphthol The reaction of the 3-formyl-4-methyl-2,6-dihydroxy pyridine with the ortho-amino-hydroxy compound is effected at elevated temperatures in suitable organic solvents, such as alcohols with 1–5 carbon atoms, glycol ethers such as ethyleneglycoldimethylether, glacial acetic acid, aprotic solvents such as toluene, carbon tetrachloride, 1,4-dioxane, tetrahydrofuran and the like, in particular in dipolar aprotic solvents, such as dimethylformamide, dimethylsulfoxide, N-methylpyrrolidone or tetramethylene sulfone and the like or in water or mixtures thereof, suitably under the atmosphere of an inert gas such as nitrogen. As reaction temperatures are suited those of 60° C. up to the reflux temperature of the solvent. Preferred reaction temperatures are those of between 80° C. and 120° C. Normally, the reaction is complete within a two to eight hours' time. The resulting azomethine can be metallized without isolation, but it is possible to carry out the isolation of the azomethine prior to its metallization. Generally, it suffices to metallize the azomethine in a suitable solvent without an isolation step. To suit this purpose, the metal-free azomethine is reacted in the solvent or solvent mixture as used in the azomethine condensation reaction with a metal salt, preferably an acetate for example a copper-(II)-acetate, under the same conditions as those prevailing in the making of the azomethine. On doing this, it may be suitable to keep the pH-value of this solution between 5 and 6, which can be done for example by adding successive amounts of a sodium acetate solution.

The metal-free azomethines are orange-colored to brown products whereas, normally, the metalliferous new metal complex compounds are olive-green and difficult or very difficult to dissolve in the conventional solvents. Therefore, the novel metal complex compounds are suited as pigments having a great coloring strength, a good resistance to solvents and temperature, especially an exceptional fastness to light and weather, for the manufacture of lacquers and varnishes, paints and printing colors as well as for the coloring of plastics in the substance and as spin-dyes. Thanks to their good fastness properties the pigments are of great interest, especially in the form of their metallic lacquers (aluminium enamels and varnishes) for high-quality exterior varnishes (automobile enamels).

The following example is illustrative, all parts and percentages being by weight unless otherwise noted:

EXAMPLE 4

21.1 g. of 2-hydroxy-3-formyl-4-methylpyridone-(6) as potassium salt are suspended together with 14.9 g. of 4-chloro-2-aminophenol in 300 ml. of glacial acetic acid and heated to the boil under a nitrogen atmosphere for three hours at about 118° C. Thereafter 10 g. of copper-II-acetate dissolved in 300 ml. of dimethylformamide are added and the temperature is kept at 140° C. for one hour.

After cooling, the reaction mixture is filtered with suction, washed with methanol and water and dried. Obtained are 33.5 g. of a yellowish-green pigment of the formula

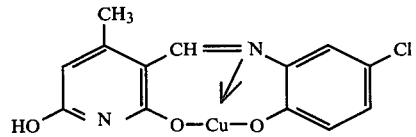

having outstanding fastness properties as to light and weather, for example in metallic (aluminium) automotive finishes.

All parts and percentages given in the following example are by weight.

EXAMPLE 5

1200 parts of water are heated to the boil and cooled down whilst passing in nitrogen gas. Thereupon 57.3 parts of 2-hydroxy-3-formyl-4-methylpyridone-(6) and 34.5 parts of o-aminophenol are added and the whole is heated for four hours under reflux, filtered hot with suction and washed with 1000 parts of water at 80° C. The resulting yellow paste of the azomethine is admixed with 6000 parts of water, 60 parts of copper(II) acetate and the mixture is heated for three and a half hours under reflux, the pH-value being kept between 5 and 6 by successive addition of 1100 parts of 10% strength sodium acetate solution. At the end of the reaction the pH-value is 5.4. The product obtained is filtered hot with suction, washed with 1200 parts of water at 80° C. and vacuum-dried at 40° C. Obtained are 44 parts of the azomethinecopper complex of the formula

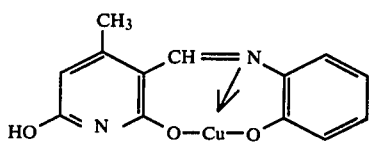

The resulting olive green pigment can be processed in the conventional manner to give a printing paste which yields prints of outstanding fastness to light.

Automotive finishes made in the conventional manner by using the pigment obtained display, after stoving, a very good fastness to light, weather and overspraying.

Analogously to the foregoing working example the metal complex compounds listed in the following Tables were made:

Table 1

| $R_4$ | $R_5$ | Me |
|---|---|---|
| 4-Cl | H | Cu |
| 4-Br | H | Cu |
| 4-$NO_2$ | H | Cu |
| 4-$CONH_2$ | H | Cu |
| 4-$CONHCH_3$ | H | Cu |
| 4-$CONHC_2H_5$ | H | Cu |
| 4-$CONHC_4H_9(n)$ | H | Cu |
| 4-$COOCH_3$ | H | Cu |
| 4-$COOC_2H_5$ | H | Cu |
| 4-$COOC_3H_7(n)$ | H | Cu |
| 4-$COOC_4H_9(n)$ | H | Cu |
| 4-$CF_3$ | H | Cu |
| 3-Cl | 5-Cl | Cu |
| 3-Br | 5-Br | Cu |
| 4-Cl | H | Co |
| 4-Br | H | Co |
| 4-Cl | H | Ni |
| 4-Br | H | Ni |
| 3-$CF_3$ | H | Co |
| 3-$CF_3$ | H | Zn |
| 5-$CF_3$ | H | Cu |
| 6-$CF_3$ | H | Cu |
| 5-$COOCH_3$ | H | Cu |
| 5-$COOCH_3$ | H | Zn |
| 5-$COOC_2H_5$ | H | Ni |
| 3-Cl | 5-$COOCH_3$ | Cu |
| 6-Br | 4-$COOC_2H_5$ | Cu |
| H | H | Co |
| H | H | Ni |
| H | H | Zn |

Table 2

| $R_4$ | $R_5$ | Me |
|---|---|---|
| 3-Br | H | Cu |
| 3-Cl | H | Cu |
| 4-Br | H | Cu |
| 4-Cl | H | Cu |

Table 2-continued

| $R_4$ | $R_5$ | Me |
|---|---|---|
| 4-$NO_2$ | H | Cu |
| 4-Cl | H | Co |
| 4-Br | H | Ni |
| 4-$NO_2$ | 8-Br | Zn |
| H | H | Cu |
| H | H | Co |
| H | H | Ni |

Table 3

| $R_4$ | $R_5$ | Me |
|---|---|---|
| H | H | Cu |
| H | H | Co |
| H | H | Zn |
| 8-Br | H | Cu |
| 8-$NO_2$ | H | Ni |
| 8-Cl | 4-Cl | Cu |

Table 4

| $R_4$ | $R_5$ | Me |
|---|---|---|
| H | H | Cu |
| H | H | Co |
| H | H | Zn |
| 4-Br | H | Cu |
| 4-Br | 8-Br | Co |
| 3-$NO_2$ | H | Cu |

The metal-free and metal-containing azomethines have a free position in the pyridine ring on which may be coupled diazo components. Thus it is possible to obtain valuable metal-free and metal-containing azomethines bearing an azo group.

Obviously many modifications and variations of the present invention are possible in the light of the above teachings. It is, therefore, to be understood that within the scope of the appended claims the invention may be practiced otherwise than as specifically described.

What is claimed:

1. A process for the production of 3-formyl-4-methyl-2,6-dihydroxy-pyridine or its alkali metal salts by reacting 4-methyl-2,6-dihydroxy-pyridine with trihaloacetaldehyde in an aqueous-ethanolic solution in the presence of sodium acetate to form 3-($\beta,\beta,\beta$-trihalo-$\alpha$-hydroxy)-ethyl-4-methyl-2,6-dihydroxy-pyridine which is hydrolized with alkali metal hydroxide in an aqueous-ethanolic solution to form haloform and 3-formyl-4-methyl-2,6-dihydroxy-pyridine as a salt of said alkali metal and recovering 3-formyl-4-methyl-2,6-dihydroxy-pyridine as the alkali metal salt.

2. A process according to claim 1 wherein free 3-formyl-4-methyl-2,6-dihydroxy-pyridine is produced by acidification of the alkali metal salt of 3-formyl-4-methyl-2,6-dihydroxy-pyridine.

* * * * *

UNITED STATES PATENT AND TRADEMARK OFFICE
CERTIFICATE OF CORRECTION

PATENT NO. : 4,157,446
DATED : June 5, 1979
INVENTOR(S) : Horst Tappe

It is certified that error appears in the above-identified patent and that said Letters Patent are hereby corrected as shown below:

Col. 3, line 28, after "(a)" change "152 parts" to

-- 15.2 --.

Col. 4, line 20, change the chemical formula to read

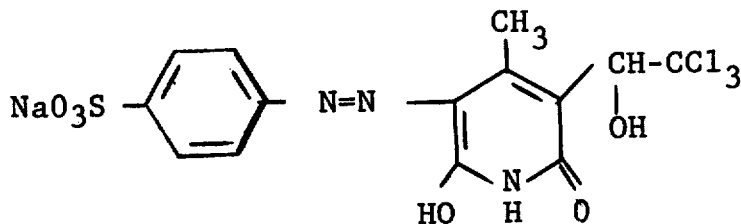

Signed and Sealed this

Fifteenth Day of July 1980

[SEAL]

Attest:

SIDNEY A. DIAMOND

Attesting Officer     Commissioner of Patents and Trademarks